United States Patent
Clarembeau et al.

[11] Patent Number: 5,849,974
[45] Date of Patent: *Dec. 15, 1998

[54] OLEFIN ISOMERIZATION PROCESS

[75] Inventors: Michel Clarembeau, Temploux; Peter Steylaerts, Keerbergen, both of Belgium

[73] Assignee: Amoco Corporation, Chicago, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 790,677

[22] Filed: Jan. 28, 1997

[30] Foreign Application Priority Data

Jan. 30, 1996 [EP] European Pat. Off. ............ 96101248

[51] Int. Cl.$^6$ .................................................. C07C 5/23
[52] U.S. Cl. ........................................... 585/668; 585/669
[58] Field of Search .................... 585/664, 665, 585/668, 669, 670

[56] References Cited

U.S. PATENT DOCUMENTS

| | | | |
|---|---|---|---|
| 4,041,090 | 8/1977 | McClure | 260/671 R |
| 4,168,284 | 9/1979 | Connor | 585/668 |
| 4,317,712 | 3/1982 | Farcasiu | 208/46 |
| 4,453,991 | 6/1984 | Grot | 156/94 |
| 4,547,474 | 10/1985 | Olah | 502/168 |
| 4,585,750 | 4/1986 | Farcasiu | 502/159 |
| 4,587,374 | 5/1986 | Peters | 585/670 |
| 4,672,147 | 6/1987 | Farcasiu | 585/668 |
| 4,673,769 | 6/1987 | Farcasiu | 585/458 |
| 4,683,216 | 7/1987 | Farcasiu | 502/159 |
| 5,104,047 | 4/1992 | Waller | 585/515 |
| 5,208,390 | 5/1993 | Onopchenko et al. | 568/766 |

FOREIGN PATENT DOCUMENTS

| | | | |
|---|---|---|---|
| 0042537 | 10/1981 | European Pat. Off. | C07C 11/02 |
| 2133962 | 4/1972 | France | C11D 1/00 |

Primary Examiner—Bekir L. Yildirim
Attorney, Agent, or Firm—James R. Henes; Stephen L. Hensley

[57] ABSTRACT

Described is a process for isomerizing α-olefin to produce olefinic oil having a viscosity at 100° C. of no more than about 1.6 cSt, a viscosity at 40° C. of no more than about 3.8 cSt, and a pour point of 0° C. or lower, preferably −10° C. or lower. The process comprises contacting the α-olefin having from about 14 to about 20 carbon atoms with a catalytic quantity of nonmetallic sulfonic or perfluorosulfonic acid resin catalyst under identified isomerization conditions, thereby producing deep internal olefin having the desired combination of physical properties.

13 Claims, 1 Drawing Sheet

OLEFIN ISOMERIZATION PROCESS

TECHNICAL FIELD

This invention pertains to novel process technology involving the production of deep internal olefins from α-olefins. More particularly, this invention pertains to a novel process of isomerizing α-olefins to produce olefinic oil having a viscosity at 100° C. of no more than about 1.6 cSt, a viscosity at 40° C. of no more than about 3.8 cSt, and a pour point of 0° C. or lower, preferably −10° C. or lower. As used herein, "olefin" means monoolefin, and the term "deep internal" with respect to olefin means that the olefin has its double bond no closer to any terminal position than the 3-position.

BACKGROUND

Hydrocarbons of various types are widely used as lubricants. In addition to mineral oils derived from petroleum, various synthetic hydrocarbon oils have been developed, including oils made by oligomerization of $C_{12}$ α-olefins. The prior art discloses that nonmetallic sulfonic acid resin catalysts and nonmetallic perfluorosulfonic acid resin catalysts act upon olefins and other compounds in certain ways, including oligomerization of olefins for lubricant stock, hydration of olefins, and hydrolysis of esters. See, for example, Watts, Jr. et al., U.S. Pat. No. 4,367,352 (1983), Butt et al., U.S. Pat. Nos. 5,094,995 (1992), 5,233,102 (1993), and 5,315,033 (1994), and Published International Application Publication Number WO 95/19222-A1 of E. I. Du Pont de Nemours and Company.

Various methods for catalytic isomerization of hydrocarbons also have been disclosed in the prior art. See, for example, Dunning, H. N., *Ind. Eng. Chem.*, 45, 551 (1953). More recently, the use of supported perfluorinated alkanesulfonic acid. subsequently bonded to a Lewis acid compound selected from higher valency fluorides of the elements of Groups IIA, IIA, IVB, VA or VIB of the Periodic Table, to isomerize certain olefins, has been described. See Olah, U.S. Pat. No. 4,547,474 (1985). Additionally, U.S. Pat. No. 5,082,986 (1992) to Miller discloses a process for reducing the pour point of a $C_{20}$+ lube oil comprising isomerizing olefins over an intermediate pore size silicoaluminophosphate molecular sieve and at least one Group VIII metal.

Recently, however, a need has arisen for a highly effective process for producing olefinic oils having low pour points while at the same time having favorable rheological properties. More particularly, a need has arisen for a process for producing olefinic oils having pour points of less than approximately 0° C., preferably −10° C. or lower, and viscosities of 1.6 cSt or less at 100° C. and 3.8 cSt or less at 40° C., as well as other physical properties useful for mud drilling and other applications, using environmentally friendly catalysts.

SUMMARY OF THE INVENTION

The present invention pertains to a new process for the production of olefinic oils possessing the above-described combination of desirable physical properties. The process employs nonmetallic sulfonic or perfluorosulfonic acid resin catalysts to facilitate the isomerization of α-olefins to deep internal olefins, despite the previously known oligomerizing characteristics of such catalysts. Such a process enables production of olefinic oil having a viscosity at 100° C. of no more than about 1.6 cSt, a viscosity at 40° C. of no more than about 3.8 cSt, and a pour point of about 0° C. or lower, and preferably about −10° C. or lower.

The process of this invention involves isomerizing α-olefin having from about 14 to about 20 carbon atoms to produce deep internal olefin having from about 14 to about 20 carbon atoms. One preferred embodiment of the invention comprises contacting the α-olefin with a catalytic quantity of a particulate sulfonic acid ion exchange resin. As used herein, particulate means finely divided, having a spherical-like or bead-like form. A second preferred embodiment of the invention comprises contacting the α-olefin with a catalytic quantity of a perfluorinated ion-exchange polymer having pendant sulfonic acid groups, such as tetrafluoroethylene/perfluoro (4-methyl-3,6-dioxa-7-octene-1-sulfonic acid) copolymer. Both types of catalysts are commercially available under various commercial trade designations. Examples of suitable sulfonic acid ion exchange resins include Amberlyst® XN1010 and Amberlyst® 36 Dry, both manufactured by Rohm & Haas Company, Philadelphia, Pa., U.S.A. An example of a suitable perfluorinated ion-exchange polymer with pendant sulfonic acid groups is Nafion® NR-50, manufactured by E. I. Du Pont de Nemours and Company.

Another preferred embodiment comprises contacting the α-olefin with a catalytic quantity of a perfluorinated ion-exchange polymer having pendant sulfonic acid groups, such as a tetrafluoroethylene/perfluoro (4-methyl-3,6-dioxa-7-octene-1-sulfonic acid) copolymer, which is supported on, or in microcomposition with, a suitable carrier, such as, for example, metal oxide or silicon oxide. Experimental versions of suitable catalysts of this type, which are apparently prepared in accordance with Published International Application Publication Number WO 95/19222-A1, may be obtained from E. I. Du Pont de Nemours and Company, under the designations Nafion® 28a (13 Wt % of supported Nafion® with the balance being silica as the carrier) and Nafion® 28b (80% Nafion® and 20% silica microcomposite), respectively. These supported catalysts are preferred as they are believed to provide greater surface area for contact between the catalyst and the olefin starting material, thereby providing for higher levels of catalytic efficiency.

DETAILED DESCRIPTION OF THE INVENTION

Figure 1:
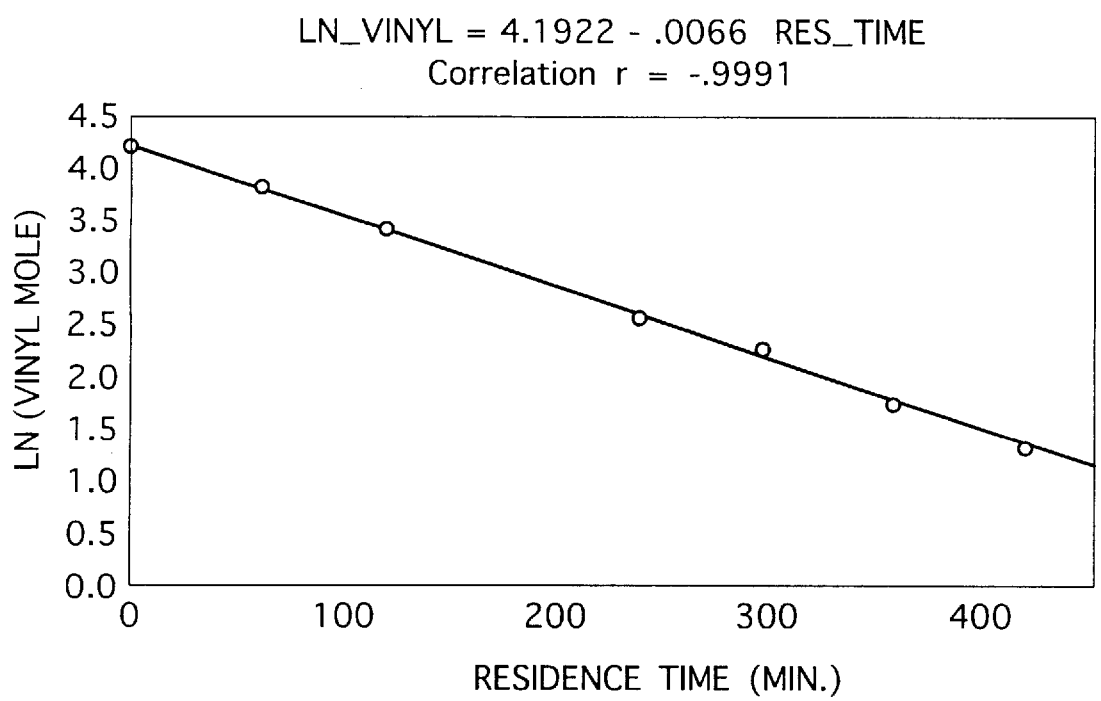
FIG. 1 is an x-y graph illustrating the linear relationship between Mol percent of linear terminal olefin and residence time for a reaction carried out under preferred conditions.

As noted above, this invention uses α-olefin starting material having anywhere from about 14 to about 20 carbon atoms per molecule, but preferably having from about 16 to about 18 carbon atoms per molecule. The starting material may contain either linear or branched olefins. In preferred forms, the starting material will be primarily (i.e., greater than 60 mol %) linear α-olefin. However, the starting material may also contain from about 10 to about 35 mol % branched α-olefin, from about 0 to about 10 mol % linear internal olefin, and/or from about 0 to about 10 mol % branched internal olefin. The α-olefin starting material also may be admixed with one or more inert hydrocarbons, such as paraffins, cycloparaffins, or aromatics. However, use of starting materials composed of at least 90% by weight olefins is preferred.

The catalyst employed in this invention may be either a sulfonic acid resin catalyst or a perfluorinated ion-exchange polymer having pendant sulfonic acid groups, and may be supported or unsupported. In a particularly preferred embodiment of the invention, the catalyst is a porous microcomposite comprising perfluorinated ion-exchange polymer having pendant sulfonic acid groups entrapped within and highly disbursed throughout a network of metal oxide, preferably silica, thereby providing increased surface area for contact between the catalyst and starting material. In this embodiment, the weight percent of polymer in the microcomposite is from about 0.1 to about 90 percent, more preferably about 0.5 to about 50 percent, and most preferably about 5 to about 25 percent, with the balance being metal oxide. The size of the pores in the microcomposite may be in the range of about 0.5 nm to about 1000 nm, with pour size in the range of about 2 to about 250 nm being more preferred.

Another preferred embodiment of the invention comprises contacting the α-olefin with a catalytic quantity of the aforesaid perfluorinated ion-exchange polymer which is itself supported on a carrier. In this embodiment, the weight percent of polymer in its supported form is from about 0.1 to about 90 percent, with the balance being carrier. In more preferred embodiments, the weight percentage is about 20 to about 85 percent, and most preferably about 60 to about 85 percent. Also in more preferred embodiments, the carrier will be a metal oxide, preferably silica. As used herein, metal oxide may include metallic or semimetallic oxide compounds, including, for example, silica, alumina, titania, germania, zirconia, alumino-silicates, zirconyl-silicates, chromic oxides, germanium oxides, copper oxides, molybdenum oxides, tantalum oxides, zinc oxides, yttrium oxides, vanadium oxides, and iron oxides.

The process may be conducted continuously, semi-continuously, or in batch operations. Preferably, the process is a continuous process for economic reasons. Various continuous processes, such as trickle beds or upflow streams, for example, may be employed to facilitate a continuous reaction while preventing formation of excessive fines when using these catalysts in supported or composite form.

The amount of catalyst used in the process varies depending upon the catalyst used. When the catalyst used is a perfluorinated ion-exchange polymer having pendant sulfonic acid groups, such as tetrafluoroethylenelperfluoro (4-methyl-3,6-dioxa-7-octene-1-sulfonic acid) copolymer, in bead form, about 100 to about 25,000 parts by weight of catalyst per million parts by weight of olefin starting material is the preferred proportion of catalyst to olefin starting material, while about 2,000 to about 8,000 parts by weight of catalyst per million parts by weight of olefin starting material is particularly preferred. About 10,000 to about 100,000 parts by weight of catalyst per million parts by weight of olefin starting material is the preferred proportion of catalyst to olefin starting material when using a particulate sulfonic acid ion-exchange resin, while about 25,000 to about 75,000 parts by weight of catalyst per million parts by weight of olefin starting material is a particularly preferred proportion. In embodiments of this invention using a perfluorinated ion-exchange polymer having pendant sulfonic acid groups, such as etrafluoroethylene/perfluoro (4-methyl-3,6-dioxa-7-octene-1-sulfonic acid) copolymer, supported on a carrier, preferably silica or another metal oxide, about 100 to about 50,000 parts by weight of supported catalyst per per million parts by weight of olefin starting material is the preferred concentration. From about 100 to about 50,000 parts by weight of catalyst per million parts by weight of olefin starting material is the preferred proportion when using a catalyst in composite with a carrier, preferably silica or another metal oxide, wherein about 0.1 to about 90 wt % is perfluorinated ion-exchange polymer having pendant sulfonic acid groups, such as tetrafluoroethylene/perfluoro (4-methyl-3,6-dioxa-7-octene-1-sulfonic acid) copolymer, with the balance being carrier. In any given case, however, higher or lower proportions of a particular catalyst may be employed depending upon the circumstances at hand and the results desired.

Typically, the isomerization reaction temperature is in the range of about 100° C. to about 175° C. In reactions using a particulate sulfonic acid ion-exchange resin for the catalyst, the temperature is preferably in the range of about 90° to about 120° C. When using a perfluorinated ion-exchange polymer having pendant sulfonic acid groups, such as tetrafluoroethylene/perfluoro (4-methyl-3,6-dioxa-7-octene-1-sulfonic acid) copolymer, the preferred temperature is in the range of about 120° to about 180° C. When the catalyst is a perfluorinated ion-exchange polymer having pendant sulfonic acid groups supported on a carrier, the preferred temperature is in the range of about 60° to about 120° C. Where such a polymer is in a porous microcomposite with a carrier, the preferred temperature will be in a range from about 60° to about 12020 C. However, departures from these temperature ranges can be used whenever deemed necessary or appropriate and are within the scope of this invention.

Pressures for the isomerization reaction may range from about 0 to about 400 bars; however, pressures in the range of from about atmospheric to about 2 bars are preferred. The process of this invention should be carried out in an inert atmosphere. Acceptable inert gases include, for example, nitrogen, argon and helium. Nitrogen is a preferred atmosphere for economical reasons.

Distillation of reaction product normally will not be required when reaction temperatures are maintained below temperatures at which catalyst degradation may occur. However, in some cases use of purification procedures may be desirable. For example, when using a perfluorinated ion-exchange resin having pendant sulfonic acid groups, such as tetrafluoroethylene/perfluoro (4-methyl-3,6-dioxa-7-octene-1-sulfonic acid) copolymer, as the catalyst, it may be desirable, especially when using higher reaction temperatures, to further purify the reaction product by vacuum distillation to remove any unwanted odors (besides the normal oily odor) or colors. Typically, such distillation may be conducted at from about 0.01 to 2 mm of Hg. However, departures from this pressure range can be used whenever deemed necessary or appropriate and are within the scope of this invention.

The following examples serve to illustrate this invention, but do not limit it. All parts are by weight unless otherwise indicated.

EXAMPLE 1

1200 Grams of olefin starting material having a ratio of 16 carbon atom olefins to 18 carbon atom olefins of 62:38, with an additional 0.3% 14 carbon atoms and 7.8% 20 or more carbon atoms, is mixed and vigorously stirred with 6 grams of Amberlyst® XN1010, described by the manufacturer as a macroreticular sulfonic acid resin catalyst, in bead form, under a nitrogen blanket at 120° C. The starting material has the following isomeric distribution: 30.5 Mol % branched olefins; 64.6 Mol % vinyl olefins; and 4.9 Mol % internal olefins. Time 0 is considered when 120° C. was reached in the reactor, and samples are withdrawn through a dip pipe to measure levels of isomerization at various reaction times. Upon monitoring with nuclear magnetic resonance, results of isomerization reactions carried out in this manner are as summarized on Table 1:

TABLE 1

| | Mol Percent (%) | | | | | |
|---|---|---|---|---|---|---|
| Type of Olefin | 0 hr. | 1 hrs. | 2 hrs. | 3 hrs. | 4 hrs. | 5 hrs. | 6 hrs. |
| Branched Terminal | 24 | 4 | 2 | 2 | 2 | 2 | 2 |
| Linear Terminal | 64 | 57 | 47 | 30 | 37 | 32 | 30 |
| Trisubstituted | 6 | 25 | 31 | 33 | 28 | 27 | 26 |
| Linear Internal | 6 | 14 | 20 | 35 | 32 | 39 | 42 |

Mol percent is estimated by measurements of olefinic nuclear magnetic resonance $^1H$ signal integers. After 6 hours, 0.8 wt % of dimer is formed.

Properties of the product obtained may be measured and compared to those properties of the starting material. This comparison is summarized in Table 2 below (as used therein and hereafter, "PMCC" stands for Penski Martin Closed Cup Method).

TABLE 2

| Properties | Isomerized Product Obtained | Starting Material |
|---|---|---|
| Viscosity at 100° C. | 1.36 cSt | 1.28 cSt |
| Viscosity at 40° C. | 3.28 cSt | 3.04 cSt |
| Pour point | −3° C. | 0° C. |
| Flash point (PMCC) | 144° C. | 141° C. |

EXAMPLE 2

1200 Grams of α-olefin starting material having isomeric distribution, in relative Mol %, of 4.5% Linear Internal Olefins, 0.0% Trisubstituted Olefins, 65% Linear Terminal Olefins, and 30.5% Branched Terminal Olefins, and having carbon number distribution of C14: 0.33; C16: 54.6; C18: 38.94; and C20: 5.25, is mixed and vigorously stirred with 5 wt % of Amberlyst® 36 Dry, described by the manufacturer as a macroreticular sulfonic acid resin catalyst, under a nitrogen blanket at 110° C. Time 0 is considered when 110° C. is reached in the reactor, and samples are withdrawn through a dip pipe to measure levels of isomerization at various reaction times. Upon monitoring with nuclear magnetic resonance, results of isomerization carried out under these conditions are as summarized on Table 3. In Table 3, and as used elsewhere herein unless otherwise defined, "Vinyl" is linear terminal olefin, "ln(Vinyl)" is the Neperian Logarithm of the vinyl mol %, "Intern." is linear internal olefin, "Trisub." is trisubstituted olefin, and "Brch." is branched terminal olefin:

TABLE 3

| Entry | Reaction time (min) | Vinyl (Mol %) | ln (Vinyl) | Intern. (Mol %) | Trisub. (Mol %) | Brch. (Mol %) |
|---|---|---|---|---|---|---|
| a | 0 | 65 | 4.174 | 4.5 | 0 | 30.5 |
| b | 360 | 33 | 3.497 | 39 | 27 | 1 |
| c | 480 | 25 | 3.219 | 47 | 27 | 1 |
| d | 600 | 11 | 2.398 | 61 | 27 | 1 |
| e | 1200 | 1 | 0 | 74 | 24 | 1 |

The linear relationship between ln(Vinyl) and reaction time is expressed in the following formula (r=correlation coefficient):

$$ln(\text{Vinyl Mol \%}) = 4.5690 - 0.0036(\text{reaction time}); \quad r = -0.9802$$

Physical properties and dimer content by gas chromatograph of entry e from Table 3 are as follows: Pour point of −12° C., Viscosity at 100° C. of 1.52 cSt, Viscosity at 40° C. of 3.83 cSt, and dimer of 9 wt %.

EXAMPLE 3

20.8 Grams of Amberlyst® 36 Dry is placed in 2 circulation columns (inner volume 2×14 mL), thermostated at a temperature of 110° C. using a Waters 410 differential refractometer column heating device. Alpha-olefin starting material having the same composition and isomeric distribution as the starting material of Example 1 is placed in a solvent dispenser, with flow rate controlled by a revamped HPLC HP1050 to allow for a continuous flow reactor. The columns are flushed for 2 hours prior to commencing flow into the reactor. The results tabulated in Table 4 indicate weight of deep internal olefins (sometimes hereafter referred to as "C1618") which are obtained at various flow rates, and certain key chemical and physical properties of the end product (as used in Table 4 and hereafter unless otherwise defined, "C32+" is weight percent of molecules having 32 or more carbon atoms, "Visc.100" is viscosity at 100° C., and "Visc.40" is viscosity at 40° C.):

TABLE 4

| Flow rate (mL/min) | Weight of C1618 (g) | C32+ (%) | Intern. (Mol %) | Trisub. (Mol %) | Vinyl (Mol %) | Brch. (Mol %) | Pour point (°C.) | Visc. 100 (cSt) | Visc. 40 (cSt) | Pressure (bars) |
|---|---|---|---|---|---|---|---|---|---|---|
| 0.35 | 605 | 1 | 64 | 26 | 9 | 1 | −12 | 1.38 | 3.35 | 23 |
| 0.5 | 2136 | 1 | 61 | 26 | 12 | 1 | −9 | 1.4 | 3.42 | 30 |
| 0.5 | 576 | — | 62 | 27 | 10 | 1 | −12 | 1.33 | 3.20 | 65 |
| 0.5 | 576 | — | 61 | 27 | 11 | 1 | −9 | 1.33 | 3.20 | 100 |
| 0.5 | 576 | — | 60 | 27 | 12 | 1 | −9 | 1.33 | 3.19 | 138 |
| 0.35 | 600 | — | 62 | 28 | 9 | 1 | −12 | 1.33 | 3.18 | 207 |

EXAMPLE 4

20.8 Grams of Amberlyst® 36 Dry is placed in 2 circulation columns (inner volume 2×14 mL), thermostated at a temperature of 110° C. using a Waters 410 differential refractometer. Alpha-olefin starting material, having the same composition and isomeric distribution as the starting material of Example 2 is placed in a solvent dispenser, with flow rate controlled by a revamped HPLC HP1050 to allow for a continuous flow reactor. The columns are flushed for 2 hours prior to commencing flow into the reactor. The results tabulated in Table 5 indicate isomeric distributions which are obtained at various flow rates.

TABLE 5

| Entry | Flow rate (ml/min) | Weight eluted (g) | Intern. (Mol %) | Trisub. (Mol %) | Vinyl (Mol %) | Brch. (Mol %) |
|---|---|---|---|---|---|---|
| a | 0.2 | 163 | 75 | 24 | 1 | 1 |
| b | 0.3 | 520 | 72 | 25 | 2 | 1 |
| c | 0.3 | 910 | 68 | 25 | 6 | 1 |
| d | 0.3 | 584 | 66 | 26 | 7 | 1 |
| e | 0.15 | 120 | 72 | 25 | 2 | 1 |

The physical properties and dimer content of the samples from the preceding table give the results set forth in Table 6:

TABLE 6

| Entry | Pour Point (°C.) | Visc. 100(cSt) | Visc.40(cSt) | Dimer(wt %) |
|---|---|---|---|---|
| a | −18 | 1.60 | 4.50 | 12 |
| b | −15 | 1.41 | 3.45 | 6 |
| c | −9 | 1.37 | 3.32 | 2 |
| d | −9 | 1.35 | 3.25 | 0.5 |
| e | −12 | 1.36 | 3.29 | 2.5 |

TABLE 7

| Type of Olefin | Mole Percent (%) | | | | | | |
|---|---|---|---|---|---|---|---|
| | 1 hr. | 3 hrs. | 66 hrs. | 92 hrs. | 98 hrs. | 122 hrs. | 140 hrs. |
| Branched Terminal | 26 | 20 | 1 | 1 | 1 | 1 | 1 |
| Linear Terminal | 67 | 65 | 23 | 16 | 16 | 11 | 9 |
| Tri-substituted | 2 | 8 | 24 | 23 | 23 | 23 | 23 |
| Linear Internal | 5 | 7 | 52 | 60 | 60 | 65 | 67 |

Mol percent is estimated by measurements of olefinic nuclear magnetic resonance $^1H$ signal integers. Approximately 0.3 wt % dimer is formed. Product has a viscosity at 100° C. of 1.36 cSt, viscosity at 40° C. of 3.31 cSt, pour point of −15° C., flash point of 136° C. (by PMCC), and a neutral oily odor.

EXAMPLE 6

24 Grams of Nafion® NR-50 in bead form are placed in 2 circulation columns (inner volume 2×14 mL) and thermostated at 150° C. using a Waters 410 differential refractometer. Alpha-olefin starting material having the same composition and isomeric distribution as the starting material of Example 1 is placed in a solvent dispenser, with flow rate controlled by a revamped HPLC HP1050 to allow for a continuous flow reactor. The columns are flushed for 2 hours prior to commencing flow into the reactor. The results set forth in Table 8 indicate weight of deep internal olefins obtained in reactions under these conditions at various flow rates, and certain key chemical and physical properties of the end product:

TABLE 8

| Flow rate (mL/min) | Weight of C1618 (g) | C32+ (%) | Intern. (Mol %) | Trisub. (Mol %) | Vinyl (Mol %) | Brch. (Mol %) | Pour point (°C.) | Visc. 100 (cSt) | Visc. 40 (cSt) | Flash Point (°C.) | Pressure (bars) |
|---|---|---|---|---|---|---|---|---|---|---|---|
| 0.3 | 240 | 5 | 63 | 28 | 8 | 1 | −15 | 1.40 | 3.45 | 130 | — |
| 0.5 | 386 | 6 | 66 | 26 | 7 | 1 | −15 | 1.41 | 3.48 | 123 | — |
| 0.7 | 646 | 7 | 66 | 27 | 6 | 1 | −18 | 1.42 | 3.53 | 123 | 44 |
| 1.5 | 1239 | 6 | 66 | 28 | 5 | 1 | −15 | 1.42 | 3.57 | 122 | — |

EXAMPLE 5

1000 Grams of α-olefin starting material, having the same composition and isomeric distribution as the starting material of Example 1 (and containing 0.0% alcohols after a scrubbing by elution on basic alumina), and 0.1 grams of Nafion® NR-50 (washed with heptane, dried 2 hours at 120° C. then placed under vacuum for 1 hour) are vigorously mixed in a batch reactor under nitrogen atmosphere at 150° C. Samples are withdrawn through a dip pipe, and indicate the isomerization over time as shown in Table 7:

EXAMPLE 7

A catalyst composed of 13 Wt % of Nafion® with the balance being silica as a carrier, having a pore size of 20 nanometers, obtained from Du Pont and apparently prepared as described in Published International Application Publication Number WO 95-19222-A1 (designated Nafion® 28a), is dried by storage in an oven at 120° C. for several days. 0.5 Wt % of the catalyst is mixed in a vigorously stirred reactor thermostated at 175° C. with 1200 g of α-olefin starting material having the same composition and isomeric distribution as the starting material of Example 2. The reaction is carried out under a nitrogen blanket. Isomeric compositions vs. reaction times for reactions carried out in this manner are given below in Table 9.

TABLE 9

| Entry | Reaction time (min.) | Vinyl (Mol %) | In (Vinyl) | Intern (Mol %) | Trisub. (Mol %) | Brch. (Mol %) |
|---|---|---|---|---|---|---|
| a | 0 | 65 | 4.174 | 4.5 | 0 | 30.5 |
| b | 30 | 7 | 1.946 | 70 | 22 | 1 |
| c | 60 | 2 | .693 | 47 | 27 | 1 |
| d | 120 | 0.1 | -2.303 | 74 | 24 | 1 |

The linear relationship between ln(Vinyl) and reaction time is expressed in the following formula:

$ln$(Vinyl Mol %)=3.8821−0.0525(reaction time); $r$=−0.9947

Entry d of Table 9 has the following physical properties and dimer content: Pour Point: −24° C.; Visc.100: 1.42 cSt; Visc.40: 3.50 cSt; Flash Pt.: 135° C. (by PMCC); Dimer: 6 wt %.

EXAMPLE 8

For two hours, an α-olefin mixture having a $C_{14}:C_{16}:C_{18}$ ratio of 59:24:17 is placed in contact with 2.5 Wt % of a dried, supported catalyst which has the same composition as, and is apparently prepared in accordance with, the catalyst of Example 7. The supported copolymer is previously dried at 120.5° C. overnight. The contact takes place within an agitated batch reactor under nitrogen blanket. The resulting internal olefin product has the following characteristics:

Gas Chromatograph Carbon Ratios ($C_{14}:C_{16}:C_{18}$): 59:25:16

Dimer: 1%

Visc.100: 1.13 cSt

Visc.40: 2.56 cSt

Flash Pt. (PMCC): 116.5° C.

Pour Point: −25.5° C.

Colour: Water clear

Odor: Neutral

Under nuclear magnetic resonance $^1$H analysis, the product has the following isomeric composition: Intern.: 80 Mol %; Trisub.: 16 Mol %; Vinyl: 3 Mol %; and Brch.: 1 Mol %.

EXAMPLE 9

0.5 Wt % of a porous microcomposite made of 80% Nafion® and 20% silica, obtained from Du Pont and apparently prepared as described in Published International Application Publication Number WO 95-19222-A1 (designated Nafion® 28b), is mixed in a vigorously stirred reactor thermostated at 175° C. with 1200 g of α-olefin starting material having the same composition and isomeric distribution as the starting material of Example 2, under a nitrogen blanket. Isomeric compositions vs. reaction times are given below in Table 10.

TABLE 10

| Entry | Reaction time (min.) | Vinyl (Mol %) | In (Vinyl) | Intern (Mol %) | Trisub. (Mol %) | Brch. (Mol %) |
|---|---|---|---|---|---|---|
| a | 0 | 65 | 4.174 | 4.5 | 0 | 30.5 |
| b | 60 | 2 | 0.693 | 47 | 27 | 1 |

Entry b of Table 10 has the following physical properties: Pour Point: −21° C.; Visc.100: 1.35 cSt; Visc.40: 3.27 cSt; Flash Pt.: 134° C. (by PMCC).

EXAMPLE 10

0.05 Wt % of a porous microcomposite which has the same composition as, and is apparently prepared in accordance with, the catalyst of Example 9 is mixed in a vigorously stirred reactor thermostated at 175° C. with 1200 g of α-olefin starting material having the same composition and isomeric distribution as the starting material of Example 2, under a nitrogen blanket. Isomeric compositions vs. reaction times are given below in Table 11.

TABLE 11

| Entry | Reaction time (min.) | Vinyl (Mol %) | In (Vinyl) | Intern (Mol %) | Trisub. (Mol %) | Brch. (Mol %) |
|---|---|---|---|---|---|---|
| a | 0 | 65 | 4.174 | 4.5 | 0 | 30.5 |
| b | 60 | 25 | 3.219 | 51 | 23 | 1 |
| c | 120 | 8 | 2.079 | 70 | 21 | 1 |
| d | 180 | 2 | .693 | 75 | 22 | 1 |

A linear relationship between ln(Vinyl) and reaction time is also observed from the data of Table 11, expressed in the following formula:

$ln$(Vinyl Mol %)=4.2789−0.0193(reaction time); $r$=−0.9965

Entry b of Table 11 has the following physical properties: Pour Point: −18° C.; Visc.100: 1.34 cSt; Visc.40: 3.21 cSt.

EXAMPLE 11

0.5 Wt % of a porous microcomposite which has the same composition as, and is apparently prepared in accordance with, the catalyst of Example 9 is mixed in a vigorously stirred reactor thermostated at 120° C. with 1200 g of α-olefin starting material having the same composition and isomeric distribution as the starting material of Example 2, under a nitrogen blanket. Isomeric compositions vs. reaction times are given below in Table 12.

TABLE 12

| Entry | Reaction time (min.) | Vinyl (Mol %) | In (Vinyl) | Intern (Mol %) | Trisub. (Mol %) | Brch. (Mol %) |
|---|---|---|---|---|---|---|
| a | 0 | 65 | 4.174 | 4.5 | 0 | 30.5 |
| b | 60 | 45 | 3.807 | 30 | 24 | 1 |
| c | 120 | 30 | 3.401 | 44 | 25 | 1 |
| d | 240 | 13 | 2.565 | 63 | 23 | 1 |
| e | 300 | 10 | 2.303 | 66 | 23 | 1 |
| f | 360 | 6 | 1.792 | 71 | 22 | 1 |
| g | 420 | 4 | 1.386 | 72 | 23 | 1 |

A linear relationship between ln(Vinyl) and reaction time is again observed from the data of Table 12, expressed in the following formula:

$ln$(Vinyl Mol %) 4.1922−0.0066(reaction time); $r$=−0.9991

A plot of this linear relationship is depicted at FIG. 1. Entry g of Table 12 has the following physical properties and dimer content: Pour Point: −15° C.; Visc.100: 1.35 cSt; Visc.40: 3.25 cSt; Flash Point: 136° C. (by PMCC); Dimer: 1 wt %.

While this invention has been described with reference to, among other things, a perfluorinated ion-exchange polymer having pendant sulfonic acid groups, a perfluorinated ion-exchange polymer having pendant carboxylic acid groups may also act to isomerize olefins in a manner similar to that described herein. This process may also have other beneficial applications in the production of alkanyl succinimide anhydride.

In accordance with the foregoing, it should be understood that each reaction described herein should be conducted under isomerization conditions, i.e., conducted within an inert atmosphere, under substantially anhydrous conditions, and at suitable pressures and temperatures as referred to hereinabove.

We claim:

1. A process of isomerizing at least one linear α-olefin having from about 14 to about 20 carbon atoms, said process comprising contacting said linear α-olefin with a catalytic quantity of a catalyst consisting essentially of supported or unsupported nonmetallic sulfonic or perfluorosulfonic acid resin catalyst, at a pressure in the range of from 0 to 400 bars and (a) at a temperature in the range of from 90° to 120° C. and at a catalyst concentration in the range of about 10,000 to about 100,000 parts by weight of catalyst per million parts of olefin starting material when the catalyst is a particulate sulfonic acid ion-exchange resin, (b) at a temperature in the range of from 120° to 180° C. and at a catalyst concentration in the range of about 100 to about 25,000 parts by weight of catalyst per million parts of olefin starting material when the catalyst is a perfluorinated ion-exchange polymer having pendant sulfonic acid groups, or (c) at a temperature in the range of from 60° to 120° C. and at a catalyst concentration in the range of about 100 to about 50,000 parts by weight of catalyst per million parts of olefin starting material when the catalyst is a perfluorinated ion-exchange polymer having pendant sulfonic acid groups either (i) supported on a carrier or (ii) in a porous microcomposite with a carrier, to thereby isomerize the linear α-olefin to form a trisubstituted olefin and only internal olefins having their double bond no closer to any terminal position than the 3-position in an olefinic oil product mixture having a viscosity at 100° C. of no more than about 1.6 cSt, a viscosity at 40° C. of no more than about 39 cSt, and a pour point of −5° C. or lower.

2. A process according to claim 1, wherein said α-olefin has from about 16 to about 18 carbon atoms.

3. A process according to claim 1, wherein said catalyst is a particulate sulfonic acid ion exchange resin.

4. A process according to claim 1, wherein said catalyst is a perfluorinated ion-exchange polymer having pendant sulfonic acid groups.

5. A process according to claim 4, wherein said catalyst is a tetrafluoroethylene/perfluoro (4-methyl-3,6-dioxa-7-octene-1-sulfonic acid) copolymer.

6. A process according to claim 4, wherein said polymer is supported on a carrier.

7. A process according to claim 6, wherein said polymer is supported on a carrier and wherein the weight percent of said polymer is about 0.1 to about 90% of the total weight of said polymer and said carrier.

8. A process according to claim 6, wherein said polymer is in the form of a porous microcomposite, wherein said polymer is entrapped within and highly disbursed throughout a carrier and has a weight percent of about 0.1 to about 90% of the total weight of said polymer and said carrier, and wherein the size of the pores in said microcomposite is about 0.5 to about 1000 nm.

9. A process according to claim 6, wherein said carrier is metal oxide.

10. A process according to claim 9, wherein said metal oxide is silica.

11. The process according to claim 1, wherein said olefinic oil has a viscosity at 100° C. of no more than about 1.5 cSt, a viscosity at 40° C. of no more than about 3.5 cSt, and a pour point of −10° C. or lower.

12. The process according to claim 1, wherein said isomerization conditions include a reaction temperature of between about 100° C. to about 175° C.

13. The product produced in accordance with claim 1.

* * * * *